(12) United States Patent
McDowell et al.

(10) Patent No.: US 6,589,288 B2
(45) Date of Patent: Jul. 8, 2003

(54) ADJUSTABLE PLUNGER PIN ASSEMBLY FOR A PROSTHETIC LIMB

(75) Inventors: Michael McDowell, Canyon, CA (US); Tracy C. Slemker, Clayton, OH (US); Scott R. Schall, Englewood, OH (US); Steve Steinbarger, Centerville, OH (US)

(73) Assignee: Prosthetic Design, Inc., Clayton, OH (US)

( * ) Notice: Subject to any disclaimer, the term of this patent is extended or adjusted under 35 U.S.C. 154(b) by 0 days.

(21) Appl. No.: 09/797,369

(22) Filed: Mar. 1, 2001

(65) Prior Publication Data

US 2002/0103544 A1 Aug. 1, 2002

Related U.S. Application Data

(60) Provisional application No. 60/265,739, filed on Feb. 1, 2001.

(51) Int. Cl.$^7$ ................................ A61F 2/60; A61F 2/74
(52) U.S. Cl. ............................................. 623/33; 623/27
(58) Field of Search .............................. 623/33, 32, 27, 623/34, 36, 28, 35, 37, 38, 39, 40

(56) References Cited

U.S. PATENT DOCUMENTS

| | | | |
|---|---|---|---|
| 5,112,356 A | 5/1992 | Harris et al. | 623/49 |
| 5,116,383 A | 5/1992 | Shorter et al. | 623/49 |
| 5,464,443 A | 11/1995 | Wilson et al. | 623/37 |
| 5,662,715 A | 9/1997 | Slemker | |
| 5,728,170 A | 3/1998 | Becker et al. | 623/37 |
| 5,888,215 A | 3/1999 | Roos et al. | 623/33 |
| 5,888,232 A * | 3/1999 | Taylor | 623/38 |
| 5,888,234 A | 3/1999 | Littig | 623/38 |
| 5,971,729 A | 10/1999 | Kristinsson et al. | 425/2 |
| 6,013,105 A | 1/2000 | Potts | |
| 6,106,559 A | 8/2000 | Meyer | 623/33 |

OTHER PUBLICATIONS

PCT International Search Report issued Jul. 2, 2002 in re International application No. PCT/US02/02918.

* cited by examiner

Primary Examiner—Corrine McDermott
Assistant Examiner—Alvin Stewart
(74) Attorney, Agent, or Firm—Taft, Stettinius & Hollister LLP

(57) ABSTRACT

A plunger pin assembly for locking engagement with a shuttle lock of a prosthetic limb socket assembly, includes: (a) a housing having an internal cavity and a center-hole extending into its distal end, communicating with the internal cavity; (b) a cradle retained within the cavity, having a distal-facing outer surface that is laterally slidable with respect to the proximal-facing inner surface of the cavity, where the cradle includes a plunger pin component extending distally therefrom; and (c) a resilient shock absorber positioned, at least partially, between the proximal end of the plunger pin component and the inner distal-facing surface of the cavity; where (d) the cradle includes a center hole extending axially therethrough, the plunger pin component includes a ball positioned on a proximal end thereof, the ball having a diameter larger than the diameter of the center hole of the cradle, and the ball of the plunger pin component is seated in the center hole of the cradle to provide a ball joint coupling between the cradle and the male coupling component. The sliding engagement between the cradle and the housing provides the plunger pin component with multiple degrees of lateral adjustability with respect to the housing, and the ball-joint coupling between the plunger pin component and the cradle provides the plunger pin component with angular and/or rotational degrees of adjustability.

58 Claims, 4 Drawing Sheets

ADJUSTABLE PLUNGER PIN ASSEMBLY FOR A PROSTHETIC LIMB

CROSS REFERENCE TO RELATED APPLICATIONS

The present application claims priority under 35 U.S.C. §119 from U.S. Provisional Patent Application Ser. No. 60/265,739, filed Feb. 1, 2001.

BACKGROUND

The present invention relates generally to prosthetic devices and, more particularly, to a male coupling component, conventionally known as a "plunger pin," extending from a sleeve or liner worn on the patient's residual limb that is adapted to lock within a female coupling component, conventionally known as a "shuttle lock," which is mounted within the rigid socket assembly of the prosthetic limb.

FIG. 1 shows a prior art socket assembly for a prosthetic limb. The prior art socket assembly includes a rigid molded plastic socket 10 sized and shaped to receive the patient's residual limb therein, a locking device 12 (such as a "shuttle lock") positioned at the distal end of the rigid socket 10, interconnection components 14 for maintaining the lock 12 within the socket and for mounting other components of the prosthetic limb to the distal end of the socket, and a silicone sleeve 16 adapted to be snugly fitted on (rolled onto) the patient's residual limb. This silicone sleeve 16 includes a plate 18 molded therein having an internally threaded boss 20 extending therefrom. A plunger pin 22 includes a externally threaded proximal end 24 adapted to be attached to the internally threaded boss 20 of the attachment plate 18 and includes a racheted distal end 26 that is adapted to be received within the center hole 28 of the lock 12 and to be locked within the center hole by a spring-loaded pawl (not shown). An example of such a silicone sleeve 16 and plunger pin 22 combination is an Alpha® Locking Liner, commercially available from the Ohio Willow Wood Company, Mt. Sterling, Ohio.

To don the prosthetic limb, a patient will roll on or slip on the silicone sleeve 16 so that the plunger pin 22 extends distally from the patient's residual limb and will then insert the residual limb into the plastic socket 10 such that the plunger pin 22 engages with the lock 12. To release the plunger pin 22 from the lock 12, a button 30 on the lock is activated to remove the pawl from within the hole 28, thereby releasing the racheted distal end 26 of the plunger pin from within the hole 28.

There are two main factors that typically cause problems with the prior art plunger pin 22 and lock 12 engagement. They are: 1) the patient has donned their locking liner 16 in a way that the plunger pin 22 is not oriented truly vertical from the center distal aspect of their limb, and 2) the lock 22 has inadvertently (during fabrication, for example) been positioned in the distal end of the socket 10 at an angle and/or dimensional offset from the distal center point. In the first case, the patient will have to re-don their locking liner 16 until the plunger pin 22 is vertical and centered on the distal end. In the second case, the socket 10 may need to be refabricated, thus positioning the lock 12 more neutrally or centered and perpendicular to the vertical axis of the limb.

SUMMARY

The present invention provides an improved plunger pin that, in an exemplary embodiment, has multiple levels of adjustability, including rotatable, pivotal and lateral adjustability. The present invention also provides a locking liner or sleeve incorporating such an adjustable plunger pin.

A first aspect of the present invention is directed to a male coupling assembly for locking engagement with a locking device of a prosthetic limb that includes: (a) a housing having an internal cavity and a center-hole extending into its distal end, communicating with the internal cavity; and (b) a cradle retained within the cavity, having a distal-facing outer surface that is laterally slidable with respect to the proximal-facing inner surface of the cavity, and the cradle including (c) a male coupling component (such as a plunger pin, for example) extending distally therefrom, where the male coupling component is adapted to be coupled to a female locking component (such as a shuttle lock, for example) of a prosthetic limb socket assembly, and further where the male coupling component extends distally through the center-hole of the housing. Therefore, cradle, and, in turn, the male coupling component is provided with, at least, multiple degrees of lateral adjustability with respect to the housing.

In a more detailed embodiment, the cradle includes a center-hole extending axially therethrough and the male coupling component includes a ball positioned on a proximal end thereof, where the ball has a diameter larger than the diameter of the center hole of the cradle, and where the ball of the male coupling component is seated in the center hole of the cradle to provide a ball joint coupling between the cradle and the male coupling component. Therefore, the male coupling component also has multiple degree of rotational and/or pivotal adjustability. In a further detailed embodiment, the male coupling assembly further includes a resilient shock absorber operatively incorporated between a male coupling component and the housing. In a more detailed embodiment, the resilient shock absorber is positioned, at least partially, between the proximal end of the male coupling component and the inner distal-facing surface of the cavity. In a further detailed embodiment, this resilient shock absorber is a cushion. In yet a further detailed embodiment, the distal-facing outer surface of the cradle has a substantially is domed shape and the proximal-facing inner surface of the cavity has a complimentary concave shape.

In an alternate detailed embodiment of the first aspect of the present invention, the distal-facing outer surface of the cradle has a substantially domed shape and the proximal-facing inner surface of the cavity has a complimentary concave shape.

In another alternate detailed embodiment of the first aspect of the present invention, the male coupled assembly further includes a fastener extending from a proximal end of the housing, which is adapted to releasably mount the male coupling assembly to a distal end of a liner, sleeve or socket worn on a patient's residual limb. In a more detailed embodiment, the fastener is an externally threaded boss that is adapted to be threaded into an internally threaded nut or projection extending from a plate integrally molded within, or otherwise attached to the liner, sleeve or socket worn on the patient's residual limb.

In another alternate detailed embodiment of the first aspect of the present invention, the housing of the male coupling assembly is integrally molded within the liner, sleeve or socket that is adapted to be worn on the patient's residual limb.

In yet another alternate detailed embodiment of the first aspect of the present invention, the housing includes a threaded outer circumferential surface that is adapted to be threaded into a threaded inner circumferential surface of a cavity extending into a distal end of the liner, sleeve or socket that is adapted to be worn on the patient's residual limb.

In yet another alternate detailed embodiment of the first aspect of the present invention the male coupling component is a shaft having a plurality of tapered annular ribs longitudinally distributed therealong, where the annular ribs taper towards the distal end of the shaft. Therefore, the male coupling component is a plunger pin adapted for engagement with a spring-loaded pawl of the female locking component. In a further detailed embodiment, the cradle includes a center hole extending axially therethrough and the shaft of the male coupling component includes a ball positioned on a proximal end thereof, the ball has a diameter larger than the diameter of the center hole of the cradle, and the ball is seated in the center hole of the cradle to provide a ball joint coupling between the cradle and the shaft of the male coupling component. Therefore, the male coupling component is provided with multiple degrees of rotational and/or pivotal adjustability. In a further detailed embodiment, the male coupling assembly further includes a resilient shock absorber operatively incorporated between the male coupling component and the housing. In yet a further detailed embodiment, the resilient shock absorber is positioned, at least partially, between the ball positioned on the proximal end of the male coupling component and the inner distal-facing surface of the cavity. In a further detailed embodiment, the resilient shock absorber is a cushion. In yet a further detailed embodiment, the distal-facing outer surface of the cradle has a substantially domed shape and the proximal-facing inner surface of the cavity has complimentary concave shape.

A second aspect of the present invention provides a male coupling assembly for locking engagement with a female locking device of a prosthetic limb that includes: (a) a base having a hole extending into its distal end and opening onto a proximal-facing surface thereof, and (b) a longitudinal male coupling component having a ball provided on the proximal end thereof, where the ball has a diameter larger than the diameter of the proximal-facing surface opening on the base; (c) where the longitudinal male coupling component extends into the proximal-facing surface opening of the hole and out through the distal end of the base, and where the ball provided at the proximal end of the longitudinal male coupling component is seated against the proximal-facing surface of the base in the proximal-facing surface opening. Therefore, a ball joint connection is provided between the longitudinal male coupling component and the base, so that the longitudinal male coupling component is provided with multiple degrees of rotational and/or pivotal adjustability with respect to the base. In a further detailed embodiment, the base includes a cavity where the proximal-facing surface opening is provided on the inner proximal-facing surface of the cavity, and the ball of the male coupling component is maintained in the cavity. In a further detailed embodiment, the male coupling assembly further includes a shock absorber positioned, at least in part, between a proximal end of the ball of the male coupling component and the inner distal-facing surface of the cavity. In yet a further detailed embodiment, the shock absorber is a cushion.

In an alternate detailed embodiment of the second aspect of the present invention, the longitudinal male coupling component is a shaft having a plurality of tapered annular ribs longitudinally distributed therealong, where the annular ribs taper towards the distal end of the shaft. Therefore, the male coupling component is adapted for engagement with a spring-loaded pawl of a female locking device of a prosthetic limb.

It is a third aspect of the present invention to provide a male coupling assembly for locking engagement with a female locking device of a prosthetic limb that includes: (a) a base, (b) a longitudinal male coupling component extending from a distal end of the base, and (c) a resilient shock absorber operatively incorporated between the longitudinal male coupling component and the base. In a more detailed embodiment, the base includes an interior cavity and a hole extending into the distal end of the base and opening into the interior cavity; the longitudinal male coupling component includes a proximal end maintained within the interior cavity, and a remaining distal portion extends out from the interior cavity, distally through the hole, and projects out through the distal end of the base; and at least a portion of the resilient shock absorber is positioned within the cavity of the base, between the proximal end of the longitudinal male coupling member and the interior, distal-facing surface of the cavity. In a more detailed embodiment, the resilient shock absorber is a cushion.

It is a fourth aspect of the present invention to provide a locking liner that is adapted to be donned onto an amputee's residual limb that includes: (a) a sleeve having an open proximal end for receiving an amputee's residual limb and a substantially closed distal end, and (b) a male coupling component extending distally from the distal end of the sleeve, where the male coupling component is adjustable in an angular, lateral or rotational orientation. In a more detailed embodiment, the male coupling component extends from a male coupling assembly that is mounted to the distal end of the sleeve.

In an alternate detailed embodiment of the fourth aspect of the present invention, the male coupling assembly includes a base from which the longitudinal male coupling component extends, and a resilient shock absorber operatively incorporated between the longitudinal male coupling component and the base. In yet another alternate detailed embodiment of the fourth aspect of the present invention, the male coupling assembly is releasably coupled to the distal end of the sleeve. In yet another alternate detailed embodiment of the fourth aspect of the present invention, the male coupling assembly is fixedly coupled to the distal end of the sleeve; where such fixedly coupling may include integrally molding the male coupling assembly within the sleeve.

It is a fifth aspect of the present invention to provide a male coupling assembly for locking engagement with a female locking device of a prosthetic limb that includes a base and a male coupling component extending from the base, where the male coupling component is coupled to the base utilizing a ball-joint connection. In a more detailed embodiment, the male coupling component includes a ball positioned on a proximal end thereof, and the ball is seated within the base. In a further detailed embodiment, the base includes at least a support component and a carriage component; the carriage component seats the ball of the male coupling component therein; and the carriage component is maintained within the support component and is laterally slidable with respect to the support component. In yet a further detailed embodiment, the male coupling assembly further includes a shock absorber operatively incorporated between the male coupling component and the base.

In an alternate detailed embodiment of the fifth aspect of the present invention, the male coupling assembly further includes a shock absorber operatively incorporated between the male coupling component and the base.

DETAILED DESCRIPTION

Figure 2:
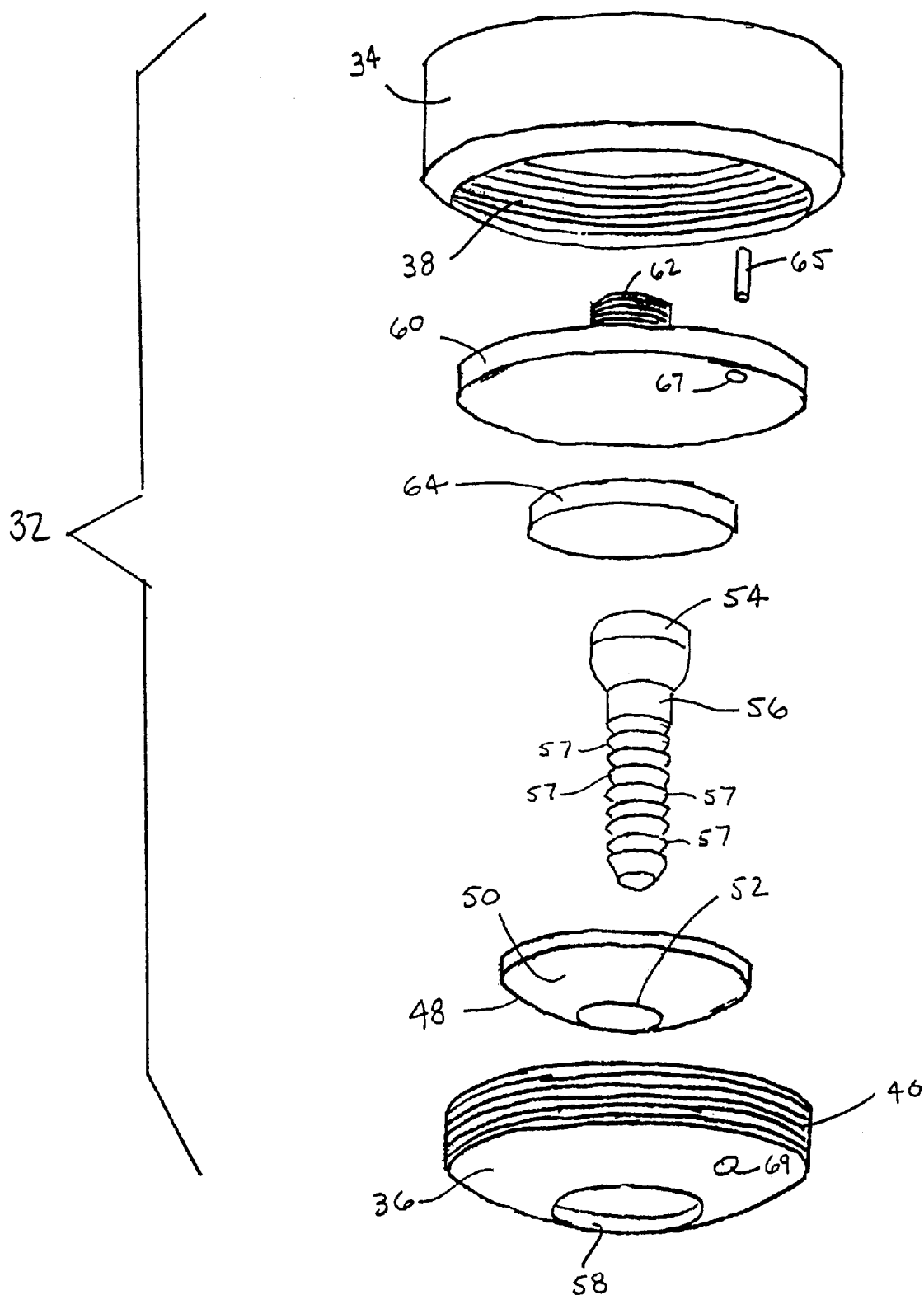
FIG. 2 provides an exploded view of the exemplary embodiment of the plunger pin assembly according to the present invention.
Figure 3:
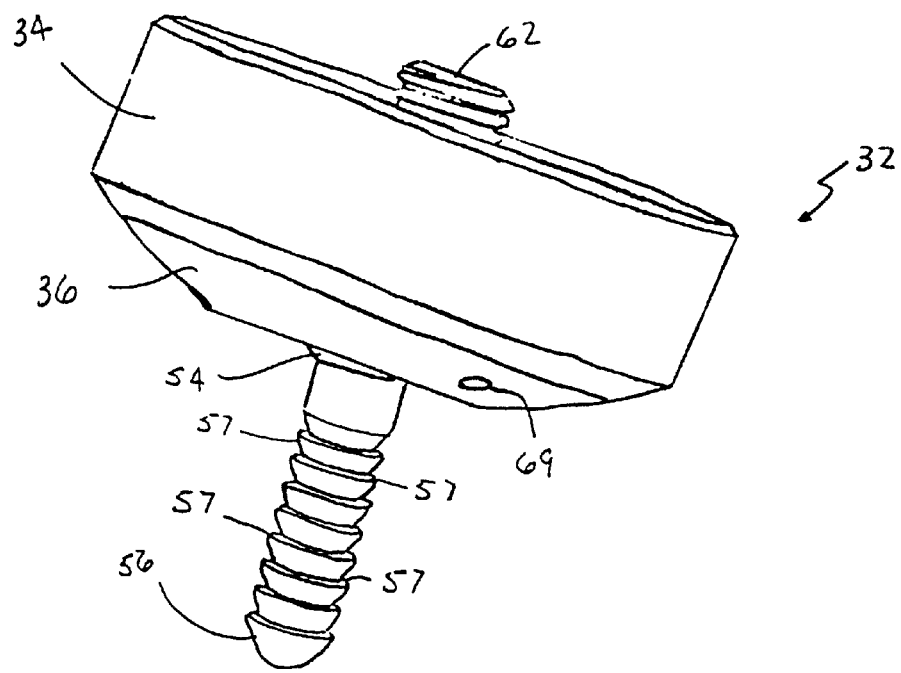
FIG. 3 provides a prospective view of the exemplary embodiment.
Figure 4:
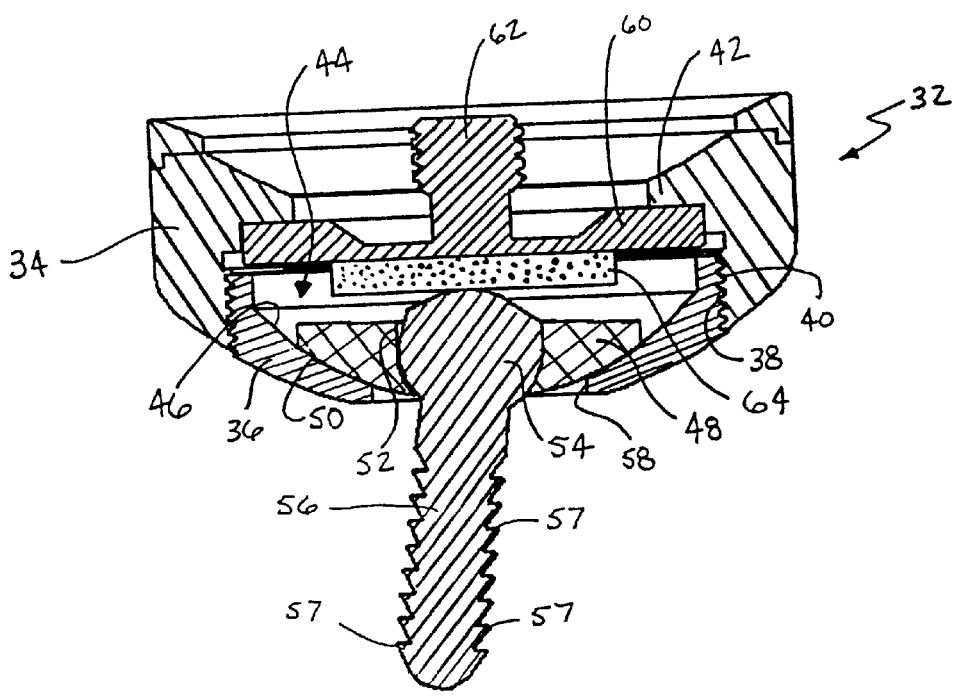
FIG. 4 provides a cross-sectional view of the exemplary embodiment.

As shown in FIGS. 2–4, an adjustable plunger pin assembly 32 according to the exemplary embodiment of the present invention includes a housing or base having an upper, annular enclosure component 34 and a lower, substantially dome shaped cap component 36. The annular enclosure component 34 includes a threaded inner circumferential surface 38 adapted to engage with the threaded outer circumferential surface 40 of the cap component 36. The annular enclosure component 34 also includes an annular shoulder 42 extending radially inward from the inner circumferential surface of the threaded center hole at a proximal end thereof. The assembled housing or base includes an interior cavity 44 with a concave inner proximal-facing surface 46. A cradle 48 is provided within the cavity 44, where the cradle has a complimentary domed distal-facing outer surface 50, which allows the cradle 48 to slide in multiple lateral directions with respect to the concave inner proximal-facing surface 46 of the cap component 36 of the housing or base. The cradle also includes a center hole 52 with a concave circumferential wall that narrows towards the distal end of the cradle. The center hole 52 retains a ball 54 provided on a proximal end of a male coupling component, which, in the exemplary embodiment is a racheted plunger pin shaft 56, having a plurality of tapered annular ribs 57 longitudinally distributed therealong, where the annular ribs 57 taper towards the distal end of the shaft 56. The plunger pin shaft 56, in turn, extends distally through an opening 58 in the distal end of the cap component 36 of the housing or base.

The ball 54 and center-hole 52 of the cradle 48 provide a ball joint connection, which in turn, provides the plunger pin shaft 56 with multiple degrees of pivotal and/or rotational adjustment with respect to the cradle 48. Furthermore, because the cradle 48 is able to slide laterally with respect to the cap 36, the cradle provide the plunger pin 56 with multiple degrees of lateral adjustment. Additionally, because the complimentary domed shapes of the outer distal-facing surface 50 of the cradle 48 and the inner proximal-facing surface 46 of the cavity 44, the cradle 48 may provide additional degrees of rotational and/or angular adjustment for the plunger pin 56.

Figure 1:
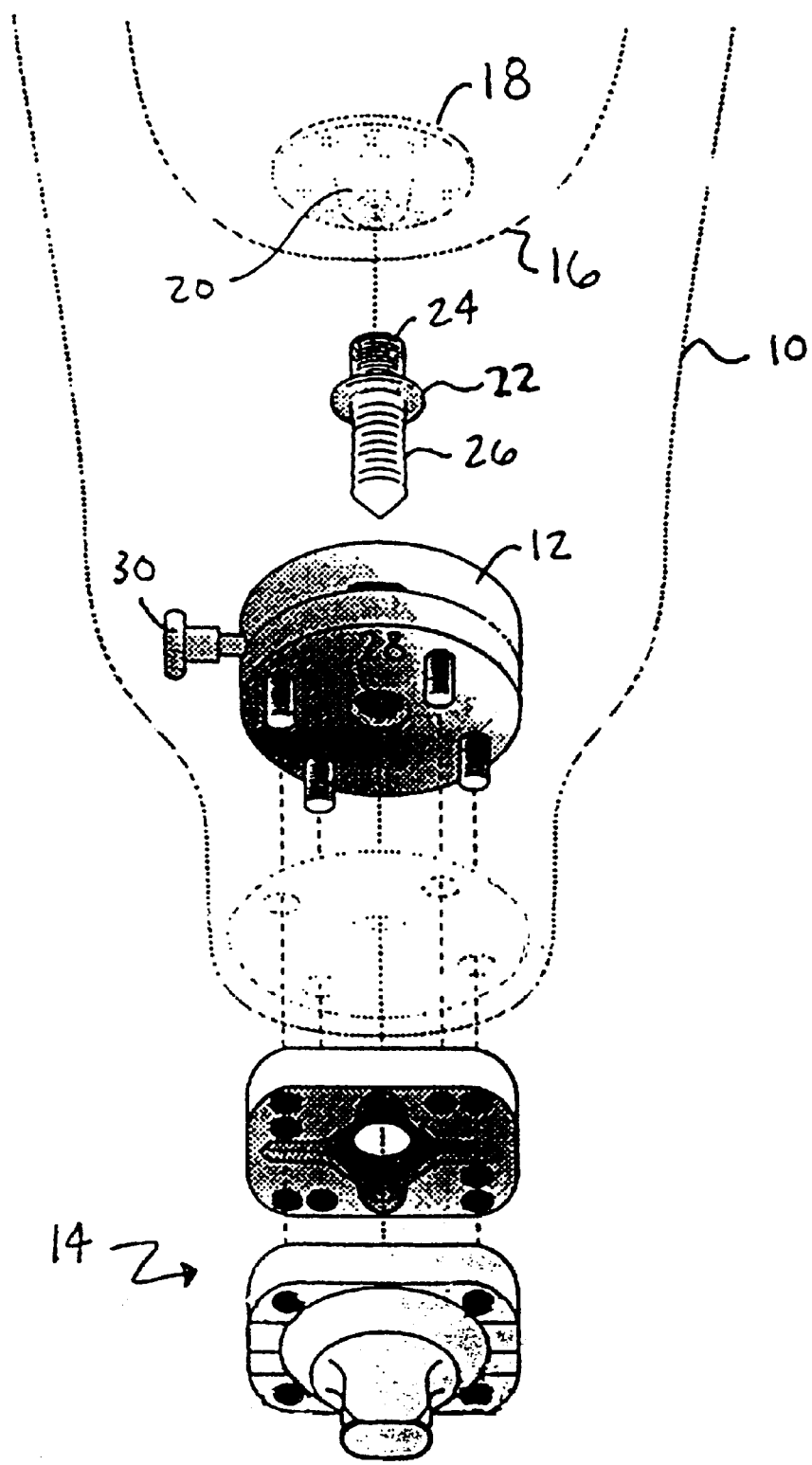
FIG. 1 shows a prior art prosthetic limb socket assembly for an above-the-knee or a below-the-knee amputee.

An attachment plate 60, having an outer diameter matching an inner diameter of the inner circumferential surface 38 of the annular enclosure component 34, is retained against the shoulder 42, axially between the cap component 36 and the shoulder 42, when the cap component 36 is threaded into the enclosure component 34. This disc-shaped plate 60 includes an externally threaded projection 62 extending proximally and concentrically therefrom, where this threaded projection 62 is adapted to be received within the internally threaded boss 20 of an attachment plate 18 molded with, or otherwise attached to the conventional sleeve or locking liner 16 as shown in FIG. 1.

A cushion 64 is provided between the distal end of the plate 60 and the proximal end of the ball 54. This cushion 64 provides a shock absorber operatively incorporated between the plunger pin 56 and the attachment plate 60, thereby absorbing shocks and vibrations experienced by the plunger pin 56 during donning or use of the prosthetic limb. As will be appreciated by those of ordinary skill in the art, it is within the scope of the invention to utilize other resilient shock absorbers in place of the cushion 64, such as a spring; or to utilize other shock absorbers that are not necessarily resilient, such as fluids contained within the cavity 44.

When the plunger pin assembly 32 has been assembled, a dowel pin 65 is inserted through a hole 67 extending axially through the attachment plate 60, such that the dowel pin 65 extends distally from the attachment plate 60 and into a hole 69 in the cap component 36. The dowel pin 65, therefore, prevents the cap component 36 from un-threading from the enclosure component 34; thereby, retaining the plunger pin assembly 32 together.

In the exemplary embodiment, the enclosure component 34, the cap component 36 and the cradle 48 are formed from a rigid plastic material; the plunger pin shaft 56 and attachment plate 60 are formed from a metal, such as titanium; and the cushion 64 is cut from a foam rubber material. Nevertheless, it will be appreciated that it is within the scope of the invention to utilize other suitable materials in place of the materials listed above.

Figure 5:
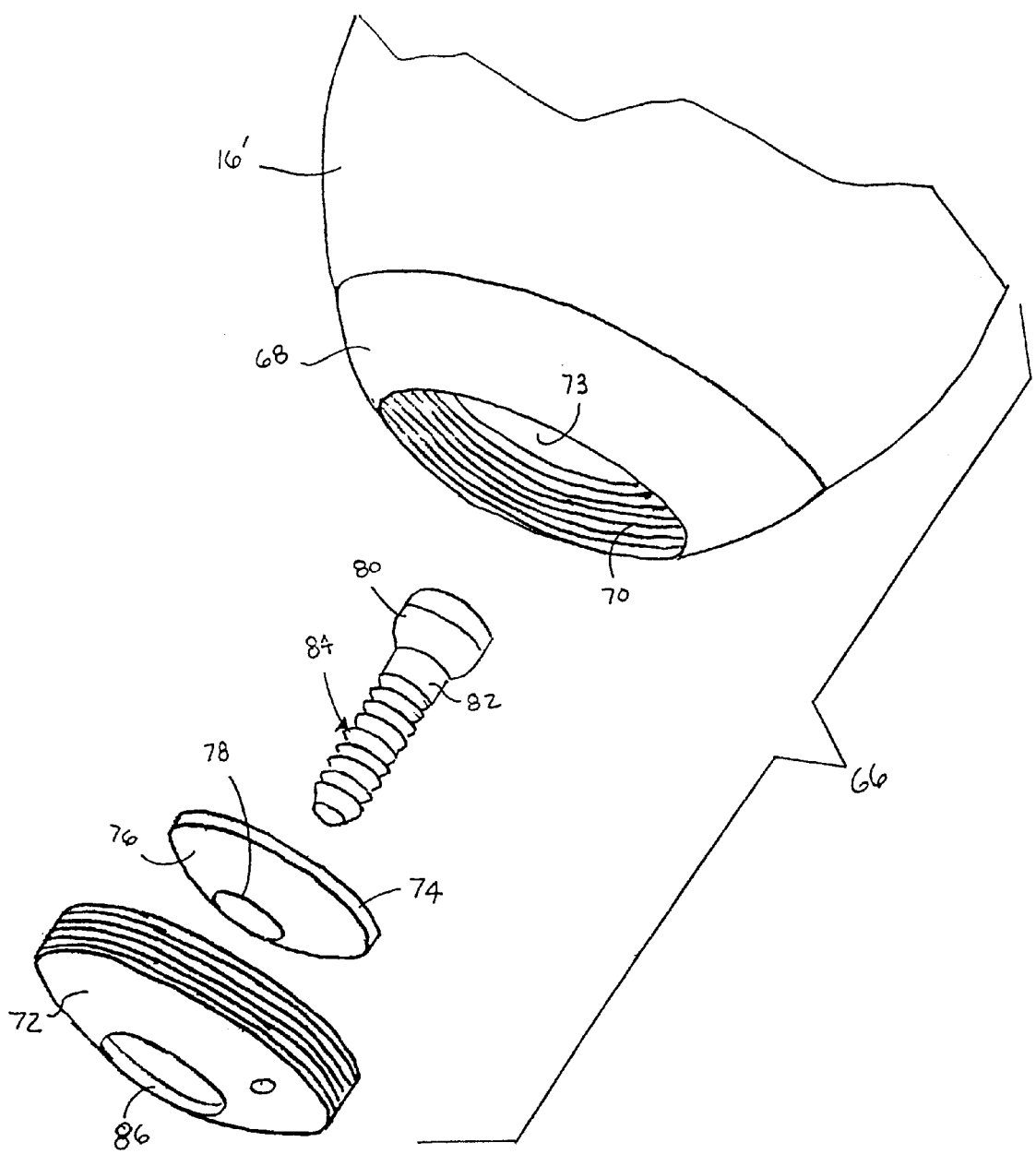
FIG. 5 shows a second exemplary embodiment of the present invention.

As shown in FIG. 5, a second exemplary embodiment of the present invention provides an adjustable plunger pin assembly 66 that is adapted to be integrated into a locking sleeve or liner 16'. The locking sleeve or liner 16' includes a plastic basket 68 molded onto or integrated with the distal end thereof, similar to the Alpha® Locking Liner commercially available from The Ohio Willow Wood Company, Mt. Sterling, Ohio. With this sleeve, however, the plastic basket 68 includes an internally threaded bore 70 adapted to receive an externally threaded cap 72, having a frustoconical shaped distal end. The bore 70 also preferably includes a closed distal-facing end surface 73. The cap 72 is similar to the cap 35 in the first exemplary embodiment and includes an interior cavity with a dome shaped or concave, proximal-facing inner surface for receiving the cradle 74 with a complimentary dome shaped, distal-facing outer surface 76 therewithin. As with the first exemplary embodiment, the cradle 74 includes a center hole 78 for retaining a ball 80 provided on a proximal end of a male coupling component, such as a racheted plunger pin shaft 82. The ball 80 and center hole 78 provide a ball joint connection, which in turn provides the plunger pin shaft 82 with multiple degrees of pivotal and/or rotational adjustment with respect to the cradle 74. Furthermore, because the cradle 74 is able to slide in lateral directions with respect to the cap 72, the cradle also provides the plunger pin shaft 82 with multiple degrees of lateral adjustment. As with the first exemplary embodiment, it is possible to incorporate a shock absorber operatively between the plunger pin shaft 82 and the basket 68, such as providing a resilient shock absorbing cushion (not shown) axially between the ball 80 and the distal-facing end surface 74 in the bore 70 of the basket 68.

The integrated adjustable plunger pin assembly 66 is assembled by positioning the plunger pin shaft 82 within the cradle 74 such that the ball 80 is received with the center hole 78 and such that the racheted portion 84 of the shaft 82 extends distally out through the hole 78 and, in turn, out through the center hole 86 of the cap 72. Thereafter, the cap 72 is threaded onto the plastic basket 68.

The second exemplary embodiment (FIG. 5) provides a reduced profile compared to the first exemplary embodiment (FIGS. 2–4). However, the first exemplary embodiment is adapted to provide a retrofit for conventional plunger pins. Additionally, it is within the scope of the invention that an adjustable plunger pin assembly, similar to the plunger pin assembly 32 of the first embodiment, may be integrally molded within a plastic basket mounted to a distal end of a sleeve or liner (similar to an Alpha® & Liner, for example). Such an integral molding of the plunger pin assembly with the sleeve or liner would also reduce the overall profile of the locking liner.

Following from the above description and invention summaries, it should be apparent to those of ordinary skill in the art that, while the apparatuses and processes herein described constitute exemplary embodiments of the present invention, it is understood that the invention is not limited to these precise apparatuses and processes and that changes may be made therein without departing from the scope of the invention as defined by the claims. Additionally, it is to be understood that the invention is defined by the claims and it is not intended that any limitations or elements describing the exemplary embodiments set forth herein are to be incorporated into the meanings of the claims unless such limitations or elements are explicitly listed in the claims. Likewise, it is to be understood that it is not necessary to meet any or all of the identified advantages or objects of the invention disclosed herein in order to fall within the scope of any claims, since the invention is defined by the claims and since inherent and/or unforeseen advantages of the present invention may exist even though they may not have been explicitly discussed herein.

What is claimed is:

1. A male coupling assembly for locking engagement with a locking device of a prosthetic limb comprising:

a housing having an internal cavity and a center-hole extending into its distal end, communicating with the internal cavity, where the cavity includes a proximal-facing inner surface and a distal-facing inner surface;

a cradle retained within the cavity, having a distal-facing outer surface that is laterally slidable with respect to the proximal-facing inner surface of the cavity, and the cradle including a male coupling component extending distally therefrom, the male coupling component being adapted to be coupled to a female locking component of a prosthetic limb socket assembly, and the male coupling component further extending distally through the center-hole of the housing;

wherein the cradle includes a center hole extending axially therethrough and the male coupling component includes a head positioned on a proximal end thereof, the head having a substantially spherical distal surface;

wherein the substantially spherical distal surface of the head has a diameter larger than the diameter of the center hole of the cradle; and wherein the head of the male coupling component is seated in the center hole of the cradle to provide a ball joint coupling between the cradle and the male coupling component;

whereby the cradle, and, in turn, the male coupling component provides, at least, multiple degrees of lateral adjustability with respect to the housing and whereby the male coupling component also has multiple degrees of rotational and/or pivotal adjustability.

2. The male coupling assembly of claim 1, wherein the distal-facing outer surface of the cradle has a substantially domed shape and the proximal-facing inner surface of the cavity has a complimentary concave shape.

3. A male coupling assembly for locking engagement with a locking device of a prosthetic limb comprising:

a housing having an internal cavity and a center-hole extending into its distal end, communicating with the internal cavity, where the cavity includes a proximal-facing inner surface and a distal-facing inner surface;

a cradle retained within the cavity, having a distal-facing outer surface that is laterally slidable with respect to the proximal-facing inner surface of the cavity, and the cradle including a male coupling component extending distally therefrom, the male coupling component being adapted to be coupled to a female locking component of a prosthetic limb socket assembly, and the male coupling component further extending distally through the center-hole of the housing; and a resilient shock absorber operatively incorporated between the male coupling component and the housing;

wherein the cradle includes a center hole extending axially therethrough and the male coupling component includes a ball positioned on a proximal end thereof;

wherein the ball has a diameter larger than the diameter of the center hole of the cradle; and the ball of the male coupling component is seated in the center hole of the cradle to provide a ball joint coupling between the cradle and the male coupling component;

whereby the cradle, and, in turn, the male coupling component provides, at least, multiple degrees of lateral adjustability with respect to the housing and whereby the male coupling component also has multiple degrees of rotational and/or pivotal adjustability.

4. The male coupling assembly of claim 3, wherein the resilient shock absorber is positioned, at least partially, between the proximal end of the male coupling component and the inner distal-facing surface of the cavity.

5. The male coupling assembly of claim 4, wherein the resilient shock absorber is a cushion.

6. The male coupling assembly of claim 5, wherein distal-facing outer surface of the cradle has a substantially domed shape and the proximal-facing inner surface of the cavity has a complimentary concave shape.

7. The male coupling assembly of claim 6, further comprising a fastener extending from a proximal end of the housing, adapted to releasably mount the male coupling assembly to a distal end of one of a liner, sleeve and socket worn on a patient's residual limb.

8. The male coupling assembly of claim 7, wherein the fastener is an externally threaded boss.

9. The male coupling assembly of claim 6, wherein the housing is integrally molded with one of a liner, sleeve and socket adapted to be worn on a patient's residual limb.

10. The male coupling assembly of claim 6, wherein the housing includes a threaded outer circumferential surface that is adapted to be threaded into a threaded inner circumferential surface of a bore extending into a distal end of one of a liner, sleeve and socket adapted to be worn on a patient's residual limb.

11. A male coupling assembly for locking engagement with a locking device of a prosthetic limb comprising:

a housing having an internal cavity and a center-hole extending into its distal end, communicating with the internal cavity, where the cavity includes a proximal-facing inner surface and a distal-facing inner surface;

a cradle retained within the cavity, having a distal-facing outer surface that is laterally slidable with respect to the proximal-facing inner surface of the cavity, and the cradle including a male coupling component extending distally therefrom, the male coupling component being adapted to be coupled to a female locking component of a prosthetic limb socket assembly, and the male coupling component further extending distally through the center-hole of the housing; and a fastener extending from a proximal end of the housing, adapted to releasably mount the male coupling assembly to a distal end of one of a liner, sleeve and socket worn on a patient's residual limb;

whereby the cradle, and, in turn, the male coupling component provides, at least, multiple degrees of lateral adjustability with respect to the housing.

12. The male coupling assembly of claim 11, wherein the fastener is an externally threaded boss.

13. A male coupling assembly for locking engagement with a locking device of a prosthetic limb comprising:

a housing having an internal cavity and a center-hole extending into its distal end, communicating with the internal cavity, where the cavity includes a proximal-facing inner surface and a distal-facing inner surface;

a cradle retained within the cavity, having a distal-facing outer surface that is laterally slidable with respect to the proximal-facing inner surface of the cavity, and the cradle including a male coupling component extending distally therefrom, the male coupling component being adapted to be coupled to a female locking component of a prosthetic limb socket assembly, and the male coupling component further extending distally through the center-hole of the housing;

wherein the housing is integrally molded with one of a liner, sleeve and socket adapted to be worn on a patient's residual limb;

whereby the cradle, and, in turn, the male coupling component provides, at least, multiple degrees of lateral adjustability with respect to the housing.

14. A male coupling assembly for locking engagement with a locking device of a prosthetic limb comprising:

a housing having an internal cavity and a center-hole extending into its distal end, communicating with the internal cavity, where the cavity includes a proximal-facing inner surface and a distal-facing inner surface;

a cradle retained within the cavity, having a distal-facing outer surface that is laterally slidable with respect to the proximal-facing inner surface of the cavity, and the cradle including a male coupling component extending distally therefrom, the male coupling component being adapted to be coupled to a female locking component of a prosthetic limb socket assembly, and the male coupling component further extending distally through the center-hole of the housing;

wherein the housing includes a threaded outer circumferential surface that is adapted to be threaded into a threaded inner circumferential surface of a bore extending into a distal end of one of a liner, sleeve and socket adapted to be worn on a patient's residual limb;

whereby the cradle, and, in turn, the male coupling component provides, at least, multiple degrees of lateral adjustability with respect to the housing.

15. A male coupling assembly for locking engagement with a locking device of a prosthetic limb comprising:

a housing having an internal cavity and a center-hole extending into its distal end, communicating with the internal cavity, where the cavity includes a proximal-facing inner surface and a distal-facing inner surface;

a cradle retained within the cavity, having a distal-facing outer surface that is laterally slidable with respect to the proximal-facing inner surface of the cavity, and the cradle including a male coupling component extending distally therefrom, the male coupling component being adapted to be coupled to a female locking component of a prosthetic limb socket assembly, and the male coupling component further extending distally through the center-hole of the housing;

wherein the male coupling component is a shaft having a distal end and a plurality of tapered annular ribs longitudinally distributed therealong, the annular ribs tapering towards the distal end of the shaft, thereby adapting the male coupling component for engagement with a spring-loaded pawl of the female locking component;

whereby the cradle, and, in turn, the male coupling component provides, at least, multiple degrees of lateral adjustability with respect to the housing.

16. The male coupling assembly of claim 15, wherein:

the cradle includes a center hole extending axially therethrough and the shaft of the male coupling component includes a ball positioned on a proximal end thereof;

the ball has a diameter larger than the diameter of the center hole of the cradle; and the ball is seated in the center hole of the cradle to provide a ball joint coupling between the cradle and the shaft of the male coupling component, thereby providing the male coupling component with multiple degrees of rotational and/or pivotal adjustability.

17. The male coupling assembly of claim 16, further comprising a resilient shock absorber operatively incorporated between the male coupling component and the housing.

18. The male coupling assembly of claim 17, wherein the resilient shock absorber is positioned, at least partially, between the ball positioned on the proximal end of the male coupling component and the inner distal-facing surface of the cavity.

19. The male coupling assembly of claim 18, wherein the resilient shock absorber is a cushion.

20. The male coupling assembly of claim 19, wherein distal-facing outer surface of the cradle has a substantially domed shape and the proximal-facing inner surface of the cavity has a complimentary concave shape.

21. A male coupling assembly for locking engagement with a female locking device of a prosthetic limb, comprising:

a base including a distal end, a proximal-facing surface and a hole extending into the distal end and opening onto the proximal-facing surface, the proximal-facing surface opening having a diameter; and a longitudinal male coupling component having a proximal end, a distal end, and a head provided on the proximal end, the head having substantially spherical distal surface with a diameter larger than the diameter of the proximal-facing surface opening;

the longitudinal male coupling component extending into the proximal-facing surface opening of the hole and out through the distal end of the base, the substantially spherical distal surface of the head provided at the proximal end of the longitudinal male coupling component being seated against the proximal-facing surface of the base in the proximal-facing surface opening, thereby providing a ball joint connection between the longitudinal male coupling component and the base so that the longitudinal male coupling component is provided with multiple degrees of rotational and/or pivotal adjustability with respect to the base.

22. The male coupling assembly of claim 21, wherein:

the base includes a cavity having an inner distal-facing surface and an inner proximal-facing surface, the proximal-facing surface opening being provided on the inner proximal-facing surface of the cavity; and the head of the male coupling component being maintained in the cavity.

23. The male coupling assembly of claim 22, wherein:

the base is an assembly of at least two components; and one of the base components is a cradle maintained within the cavity and is laterally slidable within the cavity, and the cradle includes the proximal-facing surface opening seating the substantially spherical distal surface of the head provided at the proximal end of the longitudinal male coupling component;

whereby the cradle, and, in turn, the longitudinal male coupling component is provided with multiple degrees of lateral adjustability with respect to a remainder of the base assembly.

24. A male coupling assembly for locking engagement with a female locking device of a prosthetic limb, comprising:

a base including a distal end, a proximal-facing surface and a hole extending into the distal end and opening onto the proximal-facing surface, the proximal-facing surface opening having a diameter, the base including a cavity having an inner distal-facing surface and an inner proximal-facing surface, the proximal-facing surface opening being provided on the inner proximal-facing surface of the cavity;

a longitudinal male coupling component having a proximal end, a distal end, and a ball provided on the proximal end, the ball having a diameter larger than the diameter of the proximal-facing surface opening, and the ball of the male coupling component being maintained in the cavity, the longitudinal male coupling component extending into the proximal-facing surface opening of the hole and out through the distal end of the base, the ball provided at the proximal end of the longitudinal male coupling component being seated against the proximal-facing surface of the base in the proximal-facing surface opening, thereby providing a ball joint connection between the longitudinal male coupling component and the base so that the longitudinal male coupling component is provided with multiple degrees of rotational and/or pivotal adjustability with respect to the base; and a shock absorber positioned, at least in part, between a proximal end of the ball of the male coupling component and the inner distal-facing surface of the cavity.

25. The male coupling assembly of claim 24, wherein the shock absorber is a cushion.

26. A male coupling assembly for locking engagement with a female locking device of a prosthetic limb, comprising:

a base including a distal end, a proximal-facing surface and a hole extending into the distal end and opening onto the proximal-facing surface, the proximal-facing surface opening having a diameter; and a longitudinal male coupling component having a proximal end, a distal end, and a ball provided on the proximal end, the ball having a diameter larger than the diameter of the proximal-facing surface opening;

the longitudinal male coupling component extending into the proximal-facing surface opening of the hole and out through the distal end of the base, the ball provided at the proximal end of the longitudinal male coupling component being seated against the proximal-facing surface of the base in the proximal-facing surface opening, thereby providing a ball joint connection between the longitudinal male coupling component and the base so that the longitudinal male coupling component is provided with multiple degrees of rotational and/or pivotal adjustability with respect to the base;

wherein the longitudinal male coupling component is a shaft having a plurality of tapered annular ribs longitudinally distributed therealong, the annular ribs tapering towards the distal end of the shaft, thereby adapting the male coupling component for engagement with a spring-loaded pawl of a female locking device of a prosthetic limb.

27. A male coupling assembly for locking engagement with a female locking device of a prosthetic limb, comprising:

a base;

a longitudinal male coupling component extending from a distal end of the base for locking engagement with a female locking device of a prosthetic limb; and a resilient shock absorber operatively incorporated between the longitudinal male coupling component and the base.

28. A male coupling assembly for locking engagement with a female locking device of a prosthetic limb, comprising:

a base;

a longitudinal male coupling component extending from a distal end of the base; and a resilient shock absorber operatively incorporated between the longitudinal male coupling component and the base;

wherein the base includes an interior cavity having an interior distal-facing surface, and the base further includes a hole extending into the distal end of the base and opening into the interior cavity;

wherein the longitudinal male coupling component includes a proximal end maintained within the interior cavity, and a remaining distal portion of the longitudinal male coupling component extends from the interior cavity, distally through the hole, and projects out through the distal end of the base;

and wherein at least a portion of the resilient shock absorber is positioned within the cavity of the base, between the proximal end of the longitudinal male coupling member and the interior distal-facing surface of the cavity.

29. The male coupling assembly of claim 28, wherein the resilient shock absorber is a cushion.

30. The male coupling assembly of claim 28, wherein the male coupling component is maintained within the cavity by a ball-joint coupling.

31. A male coupling assembly for locking engagement with a female locking device of a prosthetic limb, comprising:

a base;

a longitudinal male coupling component extending from a distal end of the base; and a resilient shock absorber operatively incorporated between the longitudinal male coupling component and the base;

wherein the longitudinal male coupling component is a shaft having a plurality of tapered annular ribs longitudinally distributed therealong, the annular ribs tapering towards the distal end of the shaft, thereby adapting the male coupling component for engagement with a spring-loaded pawl of a female locking device of a prosthetic limb.

32. A locking liner adapted to be donned onto an amputee's residual limb, comprising:

a sleeve having an open proximal end for receiving an amputee's residual limb and a substantially closed distal end; and a male coupling component extending distally from the distal end of the sleeve, the male coupling component being a shaft having a distal end and a plurality of tapered annular ribs longitudinally distributed therealong, the annular ribs tapering towards the distal end of the shaft, thereby adapting the male coupling component for engagement with a spring-loaded pawl of a female locking component;

the male coupling component being adjustable with respect to the distal end of the sleeve in at least one of an angular, lateral and rotational orientation.

33. A locking liner adapted to be donned onto an amputee's residual limb, comprising:

a sleeve having an open proximal end for receiving an amputee's residual limb and a substantially closed distal end; and a male coupling component extending distally from the distal end of the sleeve, the male coupling component being a shaft having a distal end and a plurality of tapered annular ribs longitudinally distributed therealong, the annular ribs tapering towards the distal end of the shaft, thereby adapting the male coupling component for engagement with a spring-loaded pawl of a female locking component;

the male coupling component being adjustable with respect to the distal end of the sleeve in at least one of an angular, lateral and rotational orientation;

wherein the male coupling component extends from a male coupling assembly mounted to the distal end of the sleeve and the male coupling component is adjustable with respect to the male coupling assembly in at least one of an angular, lateral and rotational orientation.

34. The locking liner of claim 33, wherein the male coupling assembly is releasably coupled to the distal end of the sleeve.

35. A locking liner adapted to be donned onto an amputee's residual limb, comprising:

a sleeve having an open proximal end for receiving an amputee's residual limb and a substantially closed distal end;

a male coupling assembly mounted to the distal end of the sleeve; and a male coupling component extending from the male coupling assembly and extending distally from the distal end of the sleeve, the male coupling component being adjustable in at least one of an angular, lateral and rotational orientation;

wherein the male coupling assembly includes:

a housing having an internal cavity and a center-hole extending into its distal end, communicating with the internal cavity, where the cavity includes a proximal-facing inner surface and a distal-facing inner surface; and a cradle retained within the cavity, having a distal-facing outer surface that is laterally slidable with respect to the proximal-facing inner surface of the cavity, and the cradle including the male coupling component extending distally therefrom and extending distally through the center-hole of the housing;

whereby the cradle, and, in turn, the male coupling component provides, at least, multiple degrees of lateral adjustability with respect to the housing and, in turn, the sleeve.

36. A locking liner adapted to be donned onto an amputee's residual limb, comprising:

a sleeve having an open proximal end for receiving an amputee's residual limb and a substantially closed distal end;

a male coupling assembly mounted to the distal end of the sleeve; and a male coupling component extending from the male coupling assembly and extending distally from the distal end of the sleeve, the male coupling component being adjustable in at least one of an angular, lateral and rotational orientation;

wherein the male coupling assembly includes a base having a distal end, a proximal-facing surface and a hole extending into the distal end and opening onto the proximal-facing surface, the proximal-facing surface opening having a diameter;

wherein the longitudinal male coupling component has a proximal end, a distal end, and a ball provided on the proximal end, the ball having a diameter larger than the diameter of the proximal-facing surface opening; and wherein the longitudinal male coupling component extends into the proximal-facing surface opening of the hole and out through the distal end of the base, the ball provided at the proximal end of the longitudinal male coupling component is seated against the proximal-facing surface of the base in the proximal-facing surface opening, thereby providing a ball joint connection between the longitudinal male coupling component and the base so that the longitudinal male coupling component is provided with multiple degrees of rotational and/or pivotal adjustability with respect to the base and, in turn, the sleeve.

37. A locking liner adapted to be donned onto an amputee's residual limb, comprising:

a sleeve having an open proximal end for receiving an amputee's residual limb and a substantially closed distal end;

a male coupling assembly mounted to the distal end of the sleeve; and a male coupling component extending from the male coupling assembly and extending distally from the distal end of the sleeve, the male coupling component being adjustable in at least one of an angular, lateral and rotational orientation;

wherein the male coupling assembly includes:

a base, wherein the longitudinal male coupling component extends from a distal end of the base; and a resilient shock absorber operatively incorporated between the longitudinal male coupling component and the base.

38. A locking liner adapted to be donned onto an amputee's residual limb, comprising:

a sleeve having an open proximal end for receiving an amputee's residual limb and a substantially closed distal end;

a male coupling assembly fixedly mounted to the distal end of the sleeve; and a male coupling component extending from the fixedly mounted male coupling assembly and extending distally from the distal end of the sleeve, the male coupling component being adjustable in at least one of an angular, lateral and rotational orientation with respect to the fixedly mounted male coupling assembly.

39. A locking liner adapted to be donned onto an amputee's residual limb, comprising:

a sleeve having an open proximal end for receiving an amputee's residual limb and a substantially closed distal end;

a male coupling assembly fixedly mounted to the distal end of the sleeve; and a male coupling component extending from the fixedly mounted male coupling assembly and extending distally from the distal end of the sleeve, the male coupling component being adjustable in at least one of an angular, lateral and rotational orientation with respect to the fixedly mounted male coupling assembly;

wherein the fixedly mounted male coupling assembly is integrally molded with the sleeve.

40. A male coupling assembly for locking engagement with a female locking device of a prosthetic limb, comprising a base and a male coupling component extending within the base, wherein the male coupling component includes a ball positioned on a proximal end thereof, the ball having a substantially spherical distal end, and wherein the ball is seated within the base to provide a ball-joint connection between the proximal end of the male coupling component and the base, and wherein a distal portion of the male coupling components includes a shaft having a plurality of tapered annular ribs longitudinally distributed therealong, the annular ribs tapering towards the distal end of the shaft, thereby adapting the male coupling component for engagement with a spring-loaded pawl of a female locking component.

41. A male coupling assembly for locking engagement with a female locking device of a prosthetic limb, comprising:

a base and a male coupling component extending from the base, wherein:

the male coupling component is coupled to the base utilizing a ball-joint connection;

the base includes at least a support component and a carriage component;

the carriage component seats the ball of the male coupling component therein; and the carriage component is maintained within the support component and is laterally slidable with respect to the support component.

42. The male coupling assembly of claim 41, further comprising a shock absorber operatively incorporated between the male coupling component and the base.

43. A male coupling assembly for locking engagement with a female locking device of a prosthetic limb, comprising a base and a male coupling component extending from the base, wherein the male coupling component includes a ball positioned on a proximal end thereof, the ball having a substantially spherical distal end, and wherein the ball is seated within the base to provide a ball-joint connection between the proximal end of the male coupling component and the base, the male coupling assembly further comprising a shock absorber operatively imported between the male coupling component and the base.

44. A male coupling assembly for locking engagement with a locking device of a prosthetic limb, comprising:

a housing having an internal cavity and a center-hole extending into its distal end, communicating with the internal cavity, where the cavity includes a proximal-facing inner surface and a distal-facing inner surface;

a cradle retained within the cavity, having a distal-facing outer surface that is laterally slidable with respect to the proximal-facing inner surface of the cavity, and the cradle including a male coupling component extending distally therefrom, the male coupling component being adapted to be coupled to a female locking component of a prosthetic limb socket assembly, and the male coupling component further extending distally through the center-hole of the housing; and a resilient shock absorber positioned, at least partially, between the proximal end of the male coupling component and the inner distal-facing surface of the cavity;

the cradle including a center hole extending axially therethrough;

the male coupling component including a ball positioned on a proximal end thereof, the ball having a diameter larger than the diameter of the center hole of the cradle;

the ball of the male coupling component being seated in the center hole of the cradle to provide a ball joint coupling between the cradle and the male coupling component;

whereby the sliding engagement between the cradle and the housing provides the male coupling component with multiple degrees of lateral adjustability with respect to the housing, and whereby the ball-joint coupling between the male coupling component and the cradle provides the male coupling component with angular and/or rotational degrees of adjustability.

45. The male coupling assembly of claim 44, wherein the resilient shock absorber is a cushion.

46. A locking liner adapted to be donned onto a patient's residual limb, comprising:

a resilient sleeve adapted to be snugly fitted onto a patient's residual limb, the resilient sleeve having a substantially closed distal end;

a base mounted to the distal end of the resilient sleeve; and a male coupling component, adapted for locking engagement with a female locking component of a prosthetic limb socket assembly, the male coupling component extending distally from the base and being adjustable with respect to the base in at least one of an angular, lateral and rotational orientation.

47. The locking liner of claim 46, wherein the base includes a shock absorber incorporated therein for absorbing shocks and vibrations experienced by the male coupling component during use.

48. The locking liner of claim 46, wherein the resilient sleeve is made from a resilient material including silicone.

49. The locking liner of claim 46, wherein the male coupling component is adjustable with respect to the base in at least two of an angular, lateral and rotational orientation.

50. The locking liner of claim 49, wherein the male coupling component is adjustable with respect to the base in all three of an angular, lateral and rotational orientation.

51. The locking liner of claim 46, wherein the base assembly is releasably mounted to the distal end of the resilient sleeve.

52. The locking liner of claim 51, wherein the base assembly is mounted to the distal end of the resilient sleeve by a threaded means.

53. The locking liner of claim 46, wherein the base assembly is fixedly mounted to the distal end of the resilient sleeve.

54. The locking liner of claim 53, wherein the base assembly is integrally molded with the distal end of the resilient sleeve.

55. The locking liner of claim 46, wherein the male coupling component is a shaft having a distal end and a plurality of tapered annular ribs longitudinally distributed therealong, the annular ribs tapering towards the distal end of the shaft, thereby adapting the male coupling component for engagement with a spring-loaded pawl of the female locking component.

56. The locking liner of claim 55, wherein the male coupling component is adjustable with respect to the base in at least two of an angular, lateral and rotational orientation.

57. The locking liner of claim 56, wherein the resilient sleeve is made from a resilient material including silicone.

58. The locking liner of claim 57, wherein the base includes a shock absorber incorporated therein for absorbing shocks and vibrations experienced by the male coupling component during use.

* * * * *